(12) United States Patent
Nadershahi et al.

(10) Patent No.: US 9,861,349 B2
(45) Date of Patent: Jan. 9, 2018

(54) SPECULUM FOR OBSTETRICAL AND GYNECOLOGICAL EXAMS AND RELATED PROCEDURES

(71) Applicant: Alfred E. Mann Institute for Biomedical Engineering at the University of Southern California, Los Angeles, CA (US)

(72) Inventors: Afshin Nadershahi, Northridge, CA (US); Sudeep Deshpande, Los Angeles, CA (US); Krishna Mohith Jetti, Oakbrook Terrace, IL (US)

(73) Assignee: PROA MEDICAL, INC., Redondo Beach, CA (US)

( * ) Notice: Subject to any disclaimer, the term of this patent is extended or adjusted under 35 U.S.C. 154(b) by 551 days.

(21) Appl. No.: 14/468,210

(22) Filed: Aug. 25, 2014

(65) Prior Publication Data

US 2014/0364695 A1   Dec. 11, 2014

Related U.S. Application Data

(63) Continuation-in-part of application No. 13/248,928, filed on Sep. 29, 2011, now Pat. No. 9,050,048.
(Continued)

(51) Int. Cl.
*A61B 17/02* (2006.01)
*A61B 1/32* (2006.01)
(Continued)

(52) U.S. Cl.
CPC ............ *A61B 17/0218* (2013.01); *A61B 1/32* (2013.01); *A61B 17/42* (2013.01);
(Continued)

(58) Field of Classification Search
CPC .......... A61B 1/303; A61B 1/32; A61B 17/02; A61B 17/0206; A61B 17/0218;
(Continued)

(56) References Cited

U.S. PATENT DOCUMENTS

| 55,511 A | 6/1866 | Leutz |
|---|---|---|
| 361,087 A | 4/1887 | Schenck |

(Continued)

FOREIGN PATENT DOCUMENTS

| CN | 1863479 A | 11/2006 |
|---|---|---|
| CN | 101287404 A | 10/2008 |

(Continued)

OTHER PUBLICATIONS

Cooper Surgical, Inc. 2009. Guardian Vaginal Retractor, two pages.
(Continued)

*Primary Examiner* — Christian Sevilla
*Assistant Examiner* — Eric S Gibson
(74) *Attorney, Agent, or Firm* — McDermott Will & Emery LLP

(57) ABSTRACT

This application presents structurally-adjustable vaginal specula, which provides visualization and access to the vagina and the cervix. The specula may be lightweight and compact, and may also be configured and dimensioned to minimize slippage during use. The specula may comprise built-in light sources. The specula may comprise a fluid handler, for example, to remove fluids from the vagina during medical interventions. The specula may retract the labia as well as the vaginal walls. The speculum may also be used as a retractor.

21 Claims, 15 Drawing Sheets

Related U.S. Application Data

(60) Provisional application No. 61/871,222, filed on Aug. 28, 2013, provisional application No. 61/871,229, filed on Aug. 28, 2013, provisional application No. 61/871,233, filed on Aug. 28, 2013.

(51) Int. Cl.
*A61B 17/42* (2006.01)
*A61B 17/00* (2006.01)
*A61B 90/30* (2016.01)

(52) U.S. Cl.
CPC ............ *A61B 2017/00407* (2013.01); *A61B 2017/00849* (2013.01); *A61B 2090/309* (2016.02)

(58) Field of Classification Search
CPC ............ A61B 17/42; A61B 17/4241; A61B 2017/0212; A61B 2017/0225; A61B 2017/0237; A61B 2017/0243
USPC .................................................. 600/201–249
See application file for complete search history.

(56) References Cited

U.S. PATENT DOCUMENTS

| | | | |
|---|---|---|---|
| 424,140 A | 3/1890 | Shuford | |
| 469,351 A | 2/1892 | Spanenburg | |
| 583,932 A | 6/1897 | Penderson | |
| 639,444 A | 12/1899 | Scheerer | |
| 688,935 A | 12/1901 | Crane | |
| 761,821 A | 6/1904 | Clark et al. | |
| 786,457 A | 4/1905 | McGinnis | |
| 810,675 A | 1/1906 | Richter | |
| 847,542 A | 3/1907 | Barber | |
| 977,489 A | 12/1910 | Unruh | |
| 1,014,799 A | 1/1912 | Arthur | |
| 2,012,597 A | 8/1935 | Cameron | |
| 2,374,863 A | 5/1945 | Guttmann | |
| 3,176,682 A | 4/1965 | Wexler | |
| 3,736,919 A | 6/1973 | Cotey | |
| 3,745,992 A | 7/1973 | Poirier | |
| 3,774,596 A | 11/1973 | Cook | |
| 3,789,829 A | 2/1974 | Hasson | |
| 3,796,214 A | 3/1974 | Davis | |
| 4,130,113 A | 12/1978 | Graham | |
| 4,156,424 A | 5/1979 | Burgin | |
| 4,263,898 A | 4/1981 | Wannag | |
| 4,300,541 A | 11/1981 | Burgin | |
| 4,447,227 A | 5/1984 | Kotsanis | |
| 4,754,746 A | 7/1988 | Cox | |
| 4,807,600 A | 2/1989 | Hayes | |
| 4,971,036 A | 11/1990 | Collins | |
| 5,081,983 A | 1/1992 | Villalta et al. | |
| 5,183,032 A | 2/1993 | Villalta et al. | |
| 5,209,754 A | 5/1993 | Ahluwalia | |
| 5,439,476 A | 8/1995 | Frantzides | |
| 5,465,709 A | 11/1995 | Dickie et al. | |
| 5,509,893 A | 4/1996 | Pracas | |
| RE35,312 E | 8/1996 | Christoudias | |
| 5,613,950 A | 3/1997 | Yoon | |
| 5,626,129 A | 5/1997 | Klimm et al. | |
| 5,643,285 A | 7/1997 | Rowden et al. | |
| 5,785,648 A | 7/1998 | Min | |
| 5,792,044 A | 8/1998 | Foley et al. | |
| 5,800,394 A | 9/1998 | Yoon et al. | |
| 5,868,668 A | 2/1999 | Weiss | |
| 5,894,843 A | 4/1999 | Benetti et al. | |
| 5,931,777 A | 8/1999 | Sava | |
| 5,944,736 A | 8/1999 | Taylor et al. | |
| 5,984,350 A | 11/1999 | Hagan et al. | |
| 6,024,696 A | 2/2000 | Hoftman et al. | |
| 6,024,697 A | 2/2000 | Pisarik | |
| 6,048,308 A | 4/2000 | Strong | |
| 6,096,046 A | 8/2000 | Weiss | |
| 6,196,969 B1 | 3/2001 | Bester et al. | |
| 6,265,984 B1 | 7/2001 | Molinaroli | |
| 6,280,379 B1 | 8/2001 | Resnick | |
| 6,302,842 B1 | 10/2001 | Auerbach et al. | |
| 6,312,377 B1 | 11/2001 | Segermark et al. | |
| 6,346,074 B1 | 2/2002 | Roth | |
| 6,364,832 B1 | 4/2002 | Propp | |
| 6,395,012 B1 | 5/2002 | Yoon et al. | |
| 6,416,467 B1 | 7/2002 | McMillin et al. | |
| 6,432,048 B1 | 9/2002 | Francois | |
| 6,450,952 B1 | 9/2002 | Rioux et al. | |
| 6,492,963 B1 | 12/2002 | Hoch | |
| 6,589,168 B2 | 7/2003 | Thompson | |
| 6,595,917 B2 | 7/2003 | Nieto | |
| 6,599,292 B1 | 7/2003 | Ray | |
| 6,740,031 B2 | 5/2004 | Davidson et al. | |
| 7,060,029 B1 | 6/2006 | Hajianpour | |
| 7,070,561 B1* | 7/2006 | Ansari ............... A61B 1/32 600/220 |
| 7,141,015 B2 | 11/2006 | Ruane | |
| 7,144,368 B2 | 12/2006 | Larson et al. | |
| 7,175,594 B2 | 2/2007 | Foulkes | |
| 7,248,038 B2 | 7/2007 | Wilhelmy | |
| 7,481,766 B2 | 1/2009 | Lee et al. | |
| 7,594,888 B2 | 9/2009 | Raymond et al. | |
| 7,658,712 B2 | 2/2010 | Klassen et al. | |
| 7,837,580 B2 | 11/2010 | Huang et al. | |
| 7,901,409 B2 | 3/2011 | Canaveral et al. | |
| 7,988,625 B2 | 8/2011 | Abdelgany et al. | |
| 8,409,087 B2 | 4/2013 | Ames et al. | |
| 8,409,091 B2 | 4/2013 | Blain et al. | |
| 8,449,568 B2 | 5/2013 | Nevyas-Wallace et al. | |
| 8,460,187 B2 | 6/2013 | Bouquet | |
| 8,517,935 B2 | 8/2013 | Marchek et al. | |
| 8,523,767 B2 | 9/2013 | DeRidder et al. | |
| 8,535,320 B2 | 9/2013 | Woolley et al. | |
| 8,550,994 B2 | 10/2013 | Miles et al. | |
| 8,568,306 B2 | 10/2013 | Hardenbrook | |
| 8,574,155 B2 | 11/2013 | O'Prey et al. | |
| 8,591,432 B2 | 11/2013 | Pimenta et al. | |
| 8,636,655 B1 | 1/2014 | Childs | |
| 8,696,561 B2 | 4/2014 | Fenster et al. | |
| 8,734,337 B2 | 5/2014 | Deitch et al. | |
| 8,747,308 B2 | 6/2014 | Muzzammel | |
| 8,770,200 B2 | 7/2014 | Ahluwalia | |
| 8,777,849 B2 | 7/2014 | Haig et al. | |
| 8,795,167 B2 | 8/2014 | Ainsworth et al. | |
| 8,814,789 B2 | 8/2014 | Deitch et al. | |
| 8,827,900 B1 | 9/2014 | Pimenta | |
| 8,951,226 B2 | 2/2015 | Hameed | |
| 9,050,048 B2* | 6/2015 | Nadershahi ............... A61B 1/32 |
| 9,050,058 B2 | 6/2015 | Nadershahi et al. | |
| 2002/0156350 A1 | 10/2002 | Nieto | |
| 2003/0171656 A1 | 9/2003 | Foulkes | |
| 2003/0225313 A1 | 12/2003 | Borodulin et al. | |
| 2004/0002629 A1 | 1/2004 | Branch et al. | |
| 2004/0116777 A1 | 6/2004 | Larson et al. | |
| 2005/0080320 A1* | 4/2005 | Lee ............... A61B 17/02 600/214 |
| 2005/0113644 A1 | 5/2005 | Obenchain et al. | |
| 2005/0215862 A1 | 9/2005 | Larson et al. | |
| 2005/0234304 A1 | 10/2005 | Dewey | |
| 2006/0004261 A1 | 1/2006 | Douglas | |
| 2006/0074278 A1 | 4/2006 | Petit et al. | |
| 2006/0155170 A1 | 7/2006 | Hanson et al. | |
| 2006/0235279 A1 | 10/2006 | Hawkes et al. | |
| 2007/0027364 A1 | 2/2007 | Schwer | |
| 2007/0208227 A1 | 9/2007 | Smith et al. | |
| 2007/0219416 A1 | 9/2007 | Perez-Cruet et al. | |
| 2008/0058604 A1 | 3/2008 | Sorensen | |
| 2008/0091080 A1 | 4/2008 | Leahy | |
| 2008/0214898 A1 | 9/2008 | Warren | |
| 2008/0228038 A1 | 9/2008 | McMahon et al. | |
| 2008/0245371 A1 | 10/2008 | Gruber | |
| 2008/0269565 A1 | 10/2008 | McMahon et al. | |
| 2008/0306345 A1 | 12/2008 | Balas | |
| 2009/0062042 A1 | 3/2009 | Huang et al. | |
| 2009/0076334 A1 | 3/2009 | Chen | |
| 2009/0099422 A1 | 4/2009 | George | |

(56) References Cited

U.S. PATENT DOCUMENTS

| | | |
|---|---|---|
| 2009/0198108 A1 | 8/2009 | Chen et al. |
| 2009/0259109 A1 | 10/2009 | Bucefari et al. |
| 2009/0265941 A1 | 10/2009 | Kurrus |
| 2009/0318914 A1 | 12/2009 | Utley et al. |
| 2009/0326331 A1* | 12/2009 | Rosen .................... A61B 1/303 600/224 |
| 2010/0069947 A1 | 3/2010 | Sholev et al. |
| 2010/0168523 A1 | 7/2010 | Ducharme |
| 2010/0191067 A1 | 7/2010 | Chen |
| 2010/0210901 A1 | 8/2010 | Makower et al. |
| 2010/0217091 A1 | 8/2010 | Sullivan |
| 2010/0234689 A1 | 9/2010 | Wagner et al. |
| 2010/0271010 A1 | 10/2010 | Stevens et al. |
| 2010/0305406 A1 | 12/2010 | Braun et al. |
| 2011/0021879 A1 | 1/2011 | Hart et al. |
| 2011/0201894 A1 | 8/2011 | O'Prey et al. |
| 2011/0224742 A1 | 9/2011 | Weisel et al. |
| 2012/0083658 A1* | 4/2012 | Hahn ...................... A61B 1/32 600/205 |
| 2012/0108907 A1 | 5/2012 | Fitipaldi et al. |
| 2012/0232352 A1 | 9/2012 | Lin et al. |
| 2013/0006061 A1 | 1/2013 | Alexander et al. |
| 2013/0023914 A1 | 1/2013 | Truong et al. |
| 2013/0041229 A2 | 2/2013 | Hahn et al. |
| 2013/0053863 A1 | 2/2013 | Juravic et al. |
| 2013/0103103 A1 | 4/2013 | Mire et al. |
| 2013/0190575 A1 | 7/2013 | Mast et al. |
| 2013/0274561 A1 | 10/2013 | Deitch et al. |
| 2014/0309500 A1 | 10/2014 | Thompson et al. |
| 2014/0364698 A1 | 12/2014 | Nadershahi et al. |
| 2016/0045220 A1 | 2/2016 | Wachli et al. |
| 2016/0270819 A1 | 9/2016 | Ahluwalia et al. |

FOREIGN PATENT DOCUMENTS

| | | |
|---|---|---|
| CN | 101433452 A | 5/2009 |
| CN | 102639182 A | 8/2012 |
| DE | 19828099 A1 | 12/1999 |
| SU | 167005 A1 | 1/1965 |
| SU | 1509048 A1 | 9/1989 |
| WO | 2002054961 A1 | 7/2002 |
| WO | 2004002322 A1 | 1/2004 |
| WO | 2004098416 A2 | 11/2004 |
| WO | 2009099543 A2 | 11/2004 |
| WO | 2005016131 A1 | 2/2005 |
| WO | 2006107878 A2 | 10/2006 |
| WO | WO2007075903 A2 | 7/2007 |
| WO | 2011/047066 A2 | 4/2011 |
| WO | 2012047725 A1 | 4/2012 |

OTHER PUBLICATIONS

Frankman et al. 2009. Episiotomy in the United States: has anything changed?, Am J Obstet Gyncol, vol. 200, pp. 573.e1-573.e7.
Leeman et al. 2003. Repair of Obstetric Perineal Lacerations, American Family Physician, pp. 1586-1590, vol. 68, No. 8.
Weber et al. 2002. Episiotomy Use in the United States, 1979-1997, Obstetrics & Gynecology, pp. 1177-1182, vol. 100, No. 6.
International Search Report and Written Opinion of International Searching Authority for PCT Application No. PCT/US2011/054064, filed Sep. 29, 2011, entitled "Minimally Obstructive Retractor," published Apr. 12, 2012 as WO 2012/047725 A1.

Official Action, dated May 15, 2014, from the Patent Office of the Russian Federation, for counterpart Russian Application No. 2013119383, entitled "Minimally Obstructive Retractor," national phase filing in Russia based on WO 2012/047725 (with translation and redacted cover sheet provided by Russian counsel, showing receipt date).
Extended European Search Report, dated Jul. 23, 2014, from the European Patent Office, for European Application No. 11831346.9, entitled "Minimally Obstructive Retractor," European Regional Phase filing based on WO 2012/047725.
U.S. Appl. No. 14/468,167, filed Aug. 25, 2014, entitled "Minimally Obstructive Retractor for Vaginal Repairs," Afshin Nadershahi et al., inventors.
Office Action dated Nov. 10, 2014 for U.S. Appl. No. 13/248,928, filed Sep. 29, 2011, Ricardo Hahn et al., inventors, entitled "Minimally Obstructive Retractor."
US Patent Office. 2015. Notice of Allowance, dated Feb. 28, 2015, for U.S. Appl. No. 13/248,928, entitled "Minimally Obstructive Retractor."
Communication Pursuant to Article 94(3) EPC, dated May 2, 2016, for European Application 11831346.9, entitled "Minimally Obstructive Retractor," European regional phase of PCT/US2011/054064, PCT counterpart to U.S. Appl. No. 13/248,928, now U.S. Pat. No. 9,050,048 B2.
International Search Report and Written Opinion of the US International Searching Authority (ISA/US), dated Dec. 18, 2014, for PCT Application No. PCT/US2014/052573, entitled "Minimally Obstructive Retractor for Vaginal Repairs," filed Aug. 25, 2014.
International Search Report and Written Opinion of the US International Searching Authority (ISA/US), dated Dec. 30, 2014, for PCT Application No. PCT/US2014/052574, entitled "Speculum for Obstetrical and Gynecological Exams and Related Procedures," filed Aug. 25, 2014.
Office Action, dated Jan. 12, 2015, for Chinese Application No. 201180047230.8, entitled "Minimally Obstructive Retractor," Chinese national phase of PCT/US2011/054064, PCT counterpart to U.S. Appl. No. 13/248,928.
Communication Pursuant to Article 94(3) EPC, dated Jun. 15, 2015, for European Application 11831346.9, entitled "Minimally Obstructive Retractor," European regional phase of PCT/US2011/054064, PCT counterpart to U.S. Appl. No. 13/248,928, now U.S. Pat. No. 9,050,048 B2.
Office Action, dated Jul. 28, 2015, for Chinese Application No. 201180047230.8, entitled "Minimally Obstructive Retractor," Chinese national phase of PCT/US2011/054064, PCT counterpart to U.S. Appl. No. 13/248,928, now U.S. Pat. No. 9,050,048 B2.
Office Action, dated Jul. 30, 2015, for Mexican Application No. MX/a/2013/003598, entitled "Minimally Obstructive Retractor" (memorandum with translation only) for Mexican national phase of PCT/US2011/054064, PCT counterpart to U.S. Appl. No. 13/248,928, now U.S. Pat. No. 9,050,048 B2.
Chinese Office Action from Chinese Patent Application No. 201480047470.1, dated Apr. 13, 2017.
Extended European Search Report from European Application No. 14839098.2, dated Feb. 28, 2017.
Extended European Search Report from European Application No. 14840847.9, dated Feb. 21, 2017.
Office Action dated Feb. 17, 2017, which issued in U.S. Appl. No. 14/468,167.

* cited by examiner

SPECULUM FOR OBSTETRICAL AND GYNECOLOGICAL EXAMS AND RELATED PROCEDURES

CROSS-REFERENCE TO RELATED APPLICATIONS

This application is based upon and claims priority to U.S. Provisional Patent Application Ser. No. 61/871,222, filed Aug. 28, 2013, entitled "Retractor for Vaginal Repairs"; U.S. Provisional Patent Application Ser. No. 61/871,229, filed Aug. 28, 2013, entitled "Speculum for Colposcopy"; and U.S. Provisional Patent Application Ser. No. 61/871,233, filed Aug. 28, 2013, entitled "Retractor for Surgical Incisions." This application is also a continuation-in-part of U.S. patent application Ser. No. 13/248,928, filed Sep. 29, 2011, entitled "Minimally Obstructive Retractor." The entire contents of these applications are incorporated herein by reference.

TECHNICAL FIELD

This disclosure relates generally to medical instruments, particularly structurally-adjustable speculums and retractors for gynecological and obstetrical examinations and procedures.

DESCRIPTION OF RELATED ART

In the physiological examination of the female reproductive organs, it is useful to visualize the vaginal space and the cervix. In such a physical examination, it is imperative that the view be as unobstructed and well illuminated as possible. Well illuminated visualization is also desired when procedures such as colposcopy, cervicoscopy, and endometrial ablation are performed.

For instance, Pap smears have been used regularly for diagnosing cervical cancer. Following an abnormal Pap smear, a patient is typically recommended for colposcopy (i.e., observation of the cervix). Colposcopy is a medical diagnostic procedure to examine an illuminated, magnified view of the cervix and the tissues of the vagina and vulva for signs of disease. While vaginal specula are commonly used during Pap smears and colposcopies, there are several drawbacks to existing speculum designs.

A speculum is an apparatus used for visualizing internal cavities of an individual for carrying out various diagnostic and therapeutic procedures. A vaginal speculum is a medical instrument that allows a healthcare provider to visualize and access the interior aspects of the vagina, as well as the uterine cervix. For that purpose, it is required that the speculum provide a clear path through which the internal organs may be visualized and through which some other equipment may be introduced for diagnostics and for carrying out surgical procedures.

Most existing vaginal specula comprise two blades assembled together and held by a handle. The blades and the handle form a 90-degree angle. One blade is stationary relative to the speculum handle, and the other blade pivots. As the user holds the handle, a lever attached to one blade allows it to open away from the other blade. Some designs allow the pivot point to move linearly away from the stationary blade. Nonetheless, the blades are substantially limited to moving apart and back together in relation to one axis. When the instrument is inserted into the vagina, the blades are separated in order to keep the anterior and posterior walls apart. In that position the cervix and the walls of the vagina can be seen, so long as the patient does not have excess loose vaginal tissue, and adequate illumination is provided.

Commonly used speculums are generally made of metal such as stainless steel and are designed to be sterilized between examinations. Disposable speculums are being used more and more frequently, particularly for convenience and decreased risk of transfer of contamination from one patient to another.

There are several drawbacks to existing speculum designs. The most important of these is the potential failure to fully visualize the cervix which could lead to failure to diagnose conditions such as cervical cancer. In some women, with the two-bladed speculum, the vaginal walls collapse between the two-blades and obscure the view of the cervix. This collapse of the vaginal walls between the blades of a speculum tends to occur in patients who are multiparous and those who are obese.

The multiparous patient often will have a relaxation of the levator ani musculature, which results in a tendency for the vaginal walls to collapse toward the midline during speculum examination. These muscles may be overstretched from the cumulative weight of numerous pregnancies as well as the mechanical stress of multiple vaginal deliveries.

Patients who are obese may present this internal vaginal anatomy as a result of an increase in the amount of loose connective tissue beneath the pelvic peritoneum. When these patients have a vaginal speculum examination, the loose lateral vaginal walls similarly collapse toward the midline as the blades attempt to maintain the anterior and posterior walls apart. This collapse prevents a complete and possibly crucial visualization of the cervix for the purpose of cervical cultures, pap smears, ruptured membranes, visual assessment of a degree of dilation, and biopsy.

This problem has been addressed in the past by the combined use of two instruments, one conventional speculum and a lateral retractor having two blades facing normal those of the speculum. Such usage is suggested, for example, as disclosed in a product catalog (1997) by CooperSurgical, Inc. (Trumbull, Conn.).

This problem also has been addressed by encasing the blades of a conventional speculum with a condom having its distal end removed.

Another drawback to existing speculum designs is that, when closing and removing the two-bladed speculum, there are two "pinch points" along the length of the blade members, which can cause patient discomfort upon closing of the blades in preparation for withdrawal.

Yet another drawback to existing speculum designs is that, since no part of the speculum is in direct contact with the lateral walls of the vagina, the clinician tends to open the blades wider than necessary in order to keep the lateral walls apart and conduct an adequate examination. This excessive distension of the vaginal tissue remains a source of discomfort to the patient.

Metal specula have the added drawback of conducting electricity, which can be potentially harmful to patients in certain procedures, such as loop electrosurgical excision procedure (LEEP).

In addition, the current handles on vaginal speculums are generally oriented at 90 degrees relative to the blades necessitating a specialized gynecologic table with stirrups.

Certain existing specula also require a halogen light source that is costly and requires AC/DC current. Some other speculum designs have sought to integrate lighting functions into the device. However, the various complex ways of housing light sources and delivering light to the inserts in many of these illuminated or lit specula have produced bulky and/or heavy handles and inserts, and/or maintenance issues. Furthermore, some illuminated specula have tended to emit narrow spot beams of light directed to rather small locations. As such an illuminated speculum is moved, as is often necessary, the narrow spot beam of light is concurrently (and often undesirably) moved around the cavity in various directions.

SUMMARY

This disclosure relates generally to medical instruments, particularly structurally-adjustable speculums and retractors for gynecological and obstetrical examinations and procedures.

The speculum may have a proximal end and a distal end, and an exterior surface and an interior surface. The speculum may comprise a central body portion, at least two wings, a hinge that affixes each wing to the central body portion, and a fluid handler attached to a component of the speculum. The fluid handler may remove fluid from or delivers fluid to tissue in the vicinity of the speculum during use.

The tissue may be a vaginal tissue. The speculum may be a vaginal speculum. The fluid handler may be a fluid handler that removes fluids from a vagina. The fluid handler may be a fluid handler that delivers fluids to the vagina.

The fluid handler may be attached to the central body portion. The fluid handler may be attached to at least one of the at least two wings.

The speculum may further comprise an illumination source. The fluid handler may be attached to the illumination source.

The fluid handler may comprise a conduit. The conduit may comprise a perforated segment. The conduit may also further comprise a non-perforated segment. The conduit may comprise a tube with a perforated distal end. The conduit may also comprise a tube and a perforated plate.

The speculum may further comprise a docking port, wherein the fluid handler may comprise a temporarily attachable fluid handler, and wherein the docking port may attach the temporarily attachable fluid handler to the speculum.

The speculum may further comprise a channel, and wherein the fluid handler may comprise a conduit, and wherein the conduit may comprise a non-perforated segment and a perforated segment. The central body portion may form at least a portion of the channel. The fluid handler may also form at least a portion of the channel.

The speculum may not have more than two wings and may not have more than one central body portion.

In another example, the speculum may comprise a central body portion, at least two wings, at least two hinges that affix the at least two wings to the central body portion, and wherein the distal ends of the central body portion and/or wings flare outward. The speculum may further comprise a fluid handler attached to a component of the speculum. The speculum may not have more than two wings and may not have more than one central body portion. The fluid handler may remove fluid from or delivers fluid to tissue in the vicinity of the speculum during use.

A method for a vaginal medical intervention may comprise inserting the speculum into a vagina and removing fluids from the vagina using the fluid handler. The fluid handler may be movable with respect to the central body portion, and wherein the method may further comprise re-positioning the fluid handler within the vagina after inserting the speculum.

The may further comprise repositioning the speculum after inserting the speculum by rotating the speculum within the vagina. The method may also further comprise repositioning the speculum after inserting the speculum by removing the speculum from the vagina, and then re-inserting speculum within the vagina.

The method may further comprise spreading the at least two wings apart while in the vagina. The method may further comprise closing the wings after spreading the wings and then removing the speculum from the vagina.

The method may further comprise applying a vacuum to the fluid handler.

Any combination of features and/or embodiments of the speculum and the method of its use disclosed above is within the scope of this disclosure.

It is understood that other embodiments of the devices and methods will become readily apparent to those skilled in the art from the following detailed description, wherein it is shown and described only exemplary embodiments of the devices, methods and systems by way of illustration. As will be realized, the devices, systems and systems are capable of other and different embodiments and its several details are capable of modification in various other respects, all without departing from the spirit and scope of the disclosure. Accordingly, the drawings and detailed description are to be regarded as illustrative in nature and not as restrictive.

BRIEF DESCRIPTION OF THE DRAWINGS

Aspects of the speculum are illustrated by way of example, and not by way of limitation, in the accompanying drawings.

DETAILED DESCRIPTION

Figure 1:
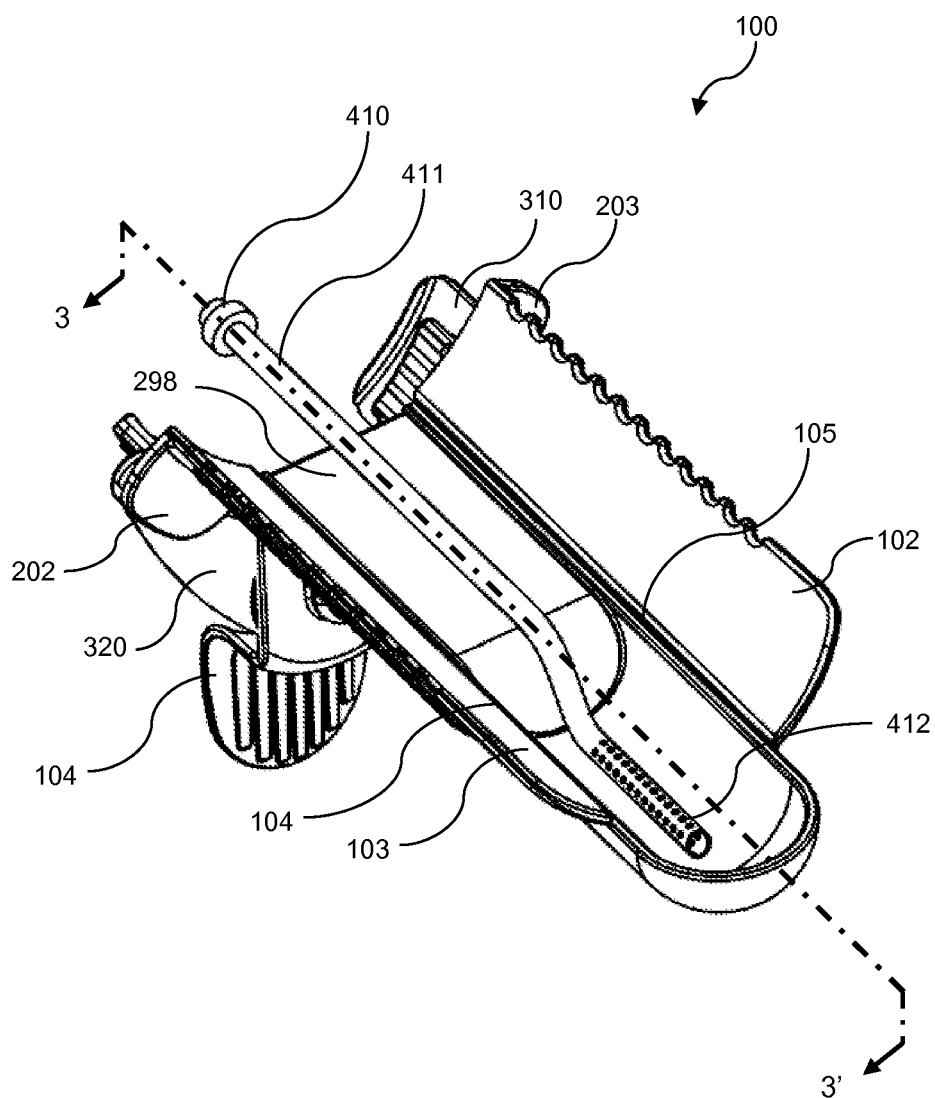
FIG. 1 is an isometric bottom view of an exemplary speculum comprising a tube perforated at its distal end.

The detailed description set forth below in connection with the appended drawings is intended as a description of exemplary embodiments and is not intended to represent the only embodiments in which the speculums and retractors can be practiced. The term "exemplary" used throughout this description means "serving as an example, instance, or illustration," and should not necessarily be construed as preferred or advantageous over other embodiments. The detailed description includes specific details for the purpose of providing a thorough understanding of the speculums/retractors. However, it will be apparent to those skilled in the art that the speculums/retractors may be practiced without these specific details.

This disclosure relates generally to medical surgical instruments, particularly structurally-adjustable speculums and retractors for gynecological and obstetrical examinations and procedures. These medical devices are hereafter called "minimally obstructive speculums" or "speculums."

Previous examples of such speculums have been disclosed, for example, by Hahn et al. in the U.S. patent application Ser. No. 13/248,928, filed Sep. 29, 2011, entitled "Minimally Obstructive Retractor." The entire content of this patent application's paragraphs [0011]-[0092] and these paragraphs' accompanying figures are incorporated herein by reference.

This instant disclosure particularly relates to a minimally obstructive speculum ("speculum") comprising a fluid handler. Examples of this speculum are shown in FIGS. 1-15. The speculum (100) has a proximal end and a distal end. The speculum (100) may comprise a central body portion (101), at least two wings (102,103), and at least one hinge (104, 105) that affixes at least one wing to the central body portion. The central body portion (101), the at least one wing (102,103), and the at least one hinge (104,105) may form a canopy.

The speculum (100) may further comprise a fluid handler (900). Some examples of the fluid handler (900) are shown in FIGS. 5, 6, 10 and 11. The fluid handler (900) may handle any type of fluid. The fluid may be gas (e.g. air), liquid (e.g. water), solid particles entrained in gas (e.g. smoke), liquid particles entrained in gas (e.g. mist), solid particles entrained in liquid, and the like. An example of the fluid is bodily fluid. Some examples of the bodily fluid may be blood, amniotic fluid, or mixtures thereof. Such bodily fluids may originate from uterus and/or cervix.

In one example, the fluid handler (900) may help to reduce the amount of fluids that may otherwise obscure inspection or interfere with a medical intervention. Examples of medical interventions may be obstetric and/or gynecological procedures. The fluid handler (900) may partially or substantially remove the fluid. For example, the fluid handler (900) may reduce the amount of bodily fluids flowing within the vagina during medical interventions. In another example, the fluid handler partially or substantially removes smoke that may form during the medical intervention to the vagina.

In another example, the fluid handler (900) may provide fluids during the medical intervention. For example, the fluid handler may provide saline for irrigation of the vagina during the medical intervention.

In one example, the fluid handler (900) may comprise a conduit. For example, the conduit may be a tube.

In another example, the fluid handler (900) may comprise a perforated conduit. For example, the fluid handler may comprise a conduit that may comprise a non-perforated segment and a perforated segment. An example of the fluid handler may comprise a tube (411) with a perforated distal end (412), as shown in FIGS. 1-6. The perforated distal end (412) may comprise one or more holes. Another example of the fluid handler may comprise a tube (411) and a perforated plate (413), as shown in FIGS. 7-11. The perforated plate (413) may comprise one or more holes. The perforated plate may have any shape. For example, the perforated plate may be curved, substantially flat, or combinations of such shapes.

The fluid handler (900) may further comprise a fluid handler port (410), which may be used to attach, for example a pump, to handle the fluids. The pump (not shown in the figures) may be used to remove or provide fluids, for example, to the vagina. The pump may be a vacuum pump.

The fluid handler (900) may be permanently attached to the speculum (100), as shown in FIGS. 1-4, 7-8 and 15. The fluid handler (900) may be temporarily attached to the speculum (100), as shown in FIGS. 5-6 and 10-11. In one example, the fluid handler may be permanently attached to the central body portion. In another example, the fluid handler may be permanently attached to at least one of the wings.

Figure 5:
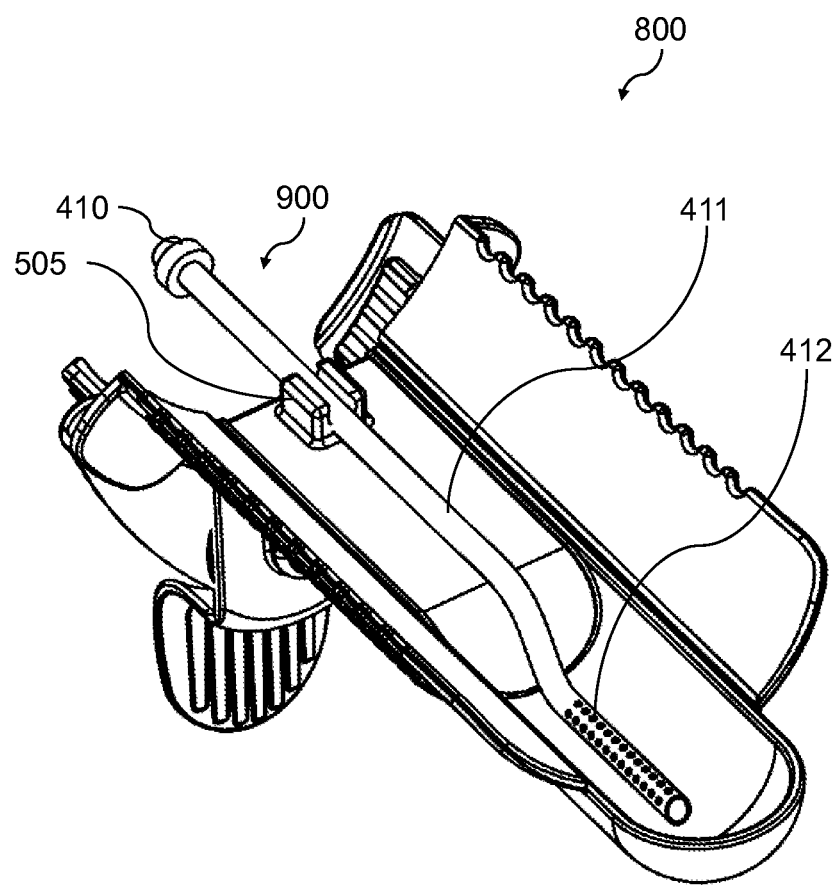
FIG. 5 is an isometric bottom view of an exemplary speculum comprising a tube perforated at its distal end.
Figure 6:
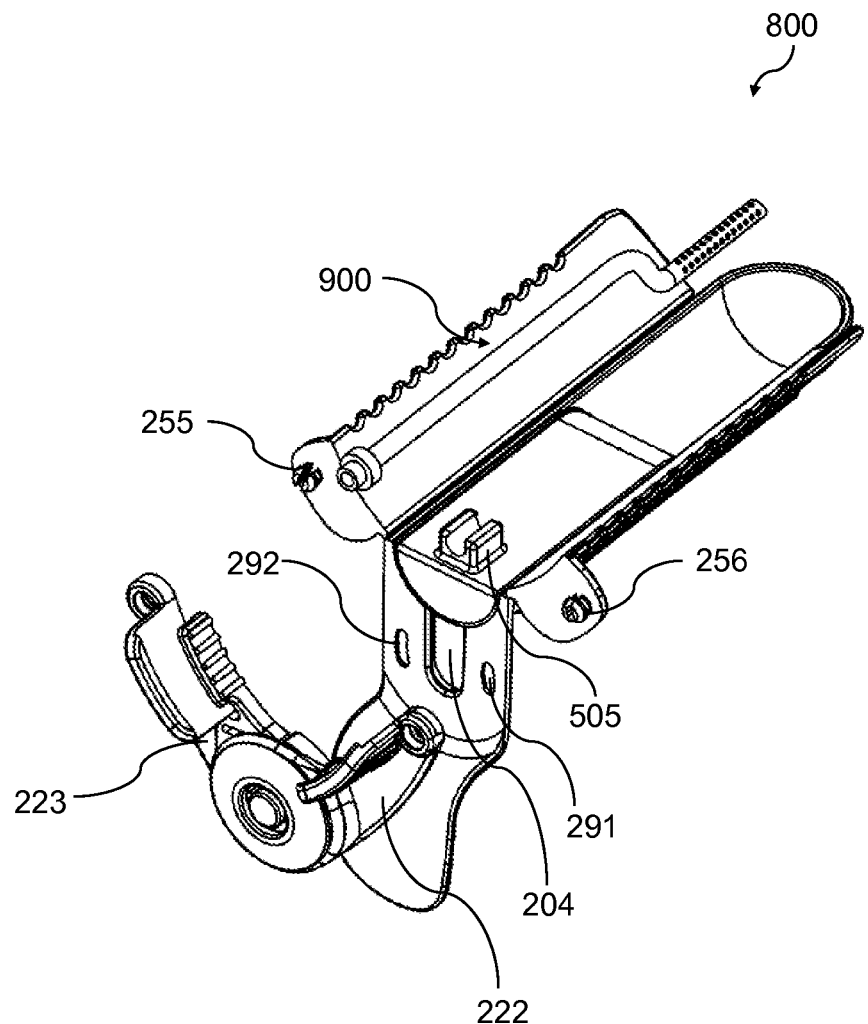
FIG. 6 is an exploded bottom view of the exemplary speculum of FIG. 5 with the tube detached.
Figure 7:
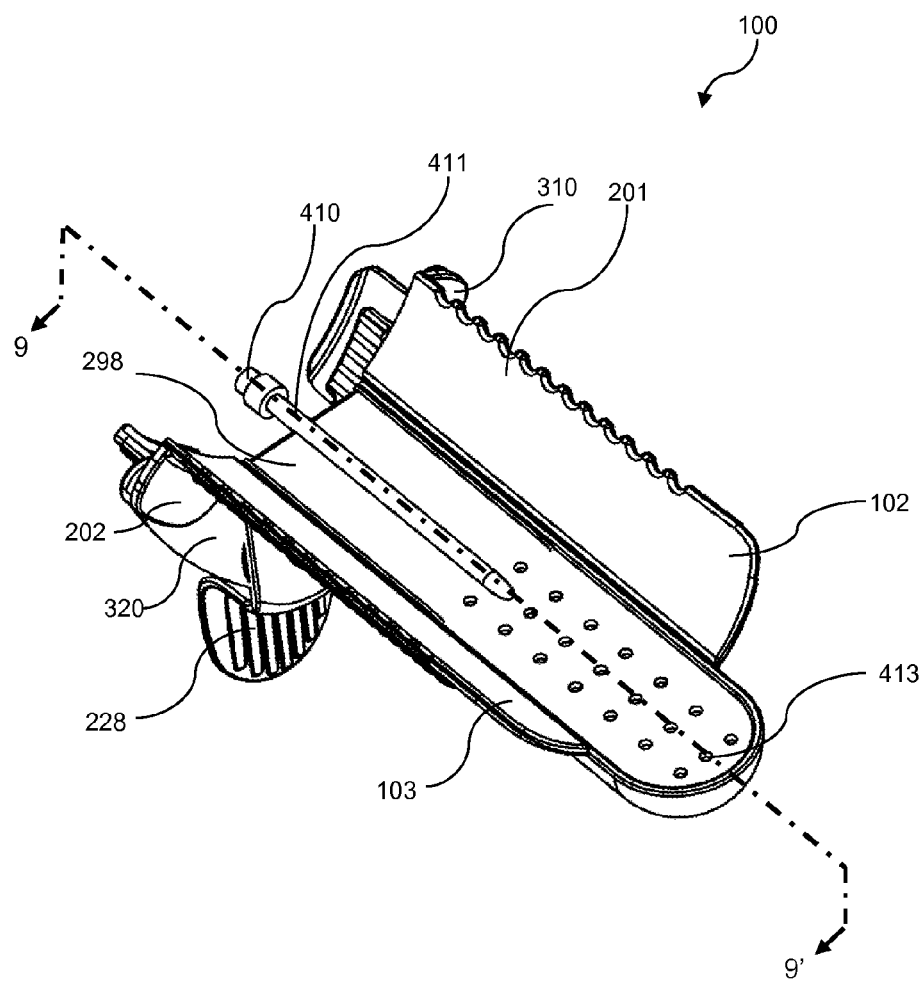
FIG. 7 is an isometric bottom view of an exemplary speculum comprising a perforated plate.

In one example, the speculum (100) may further comprise a docking port to securely attach the fluid handler (900) to the speculum (100), as shown in FIG. 5. The docking port may temporarily hold the fluid handler against the speculum (100) such that the fluid handler does not obstruct the user from performing inspection or procedures upon the vaginal walls or surrounding anatomic structures. Examples of the docking ports may be clips, fasteners, loops, hooks, adhesive pads, and combinations thereof. In one example, the fluid handler (900) may be a temporarily attachable fluid handler. In this example, the tube (411) of the fluid handler (900) may temporarily be attached or docked onto the speculum (100) by using a clip (505), as shown in FIGS. 5, 6, 10 and 11. In one example, the fluid handler may be temporarily attached to the central body portion. In another example, the fluid handler may be temporarily attached to at least one of the wings.

Figure 2:
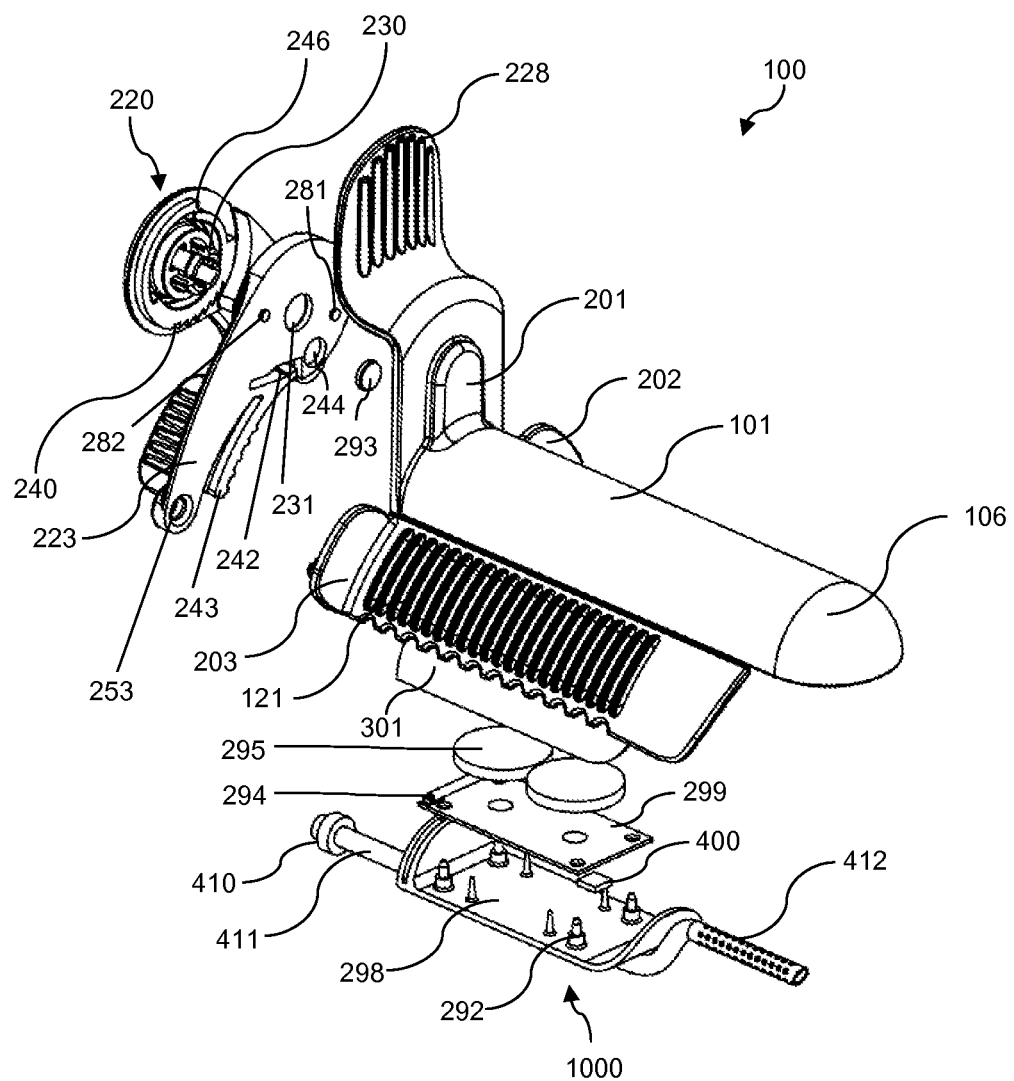
FIG. 2 is an exploded top view of the exemplary speculum of FIG. 1
Figure 8:
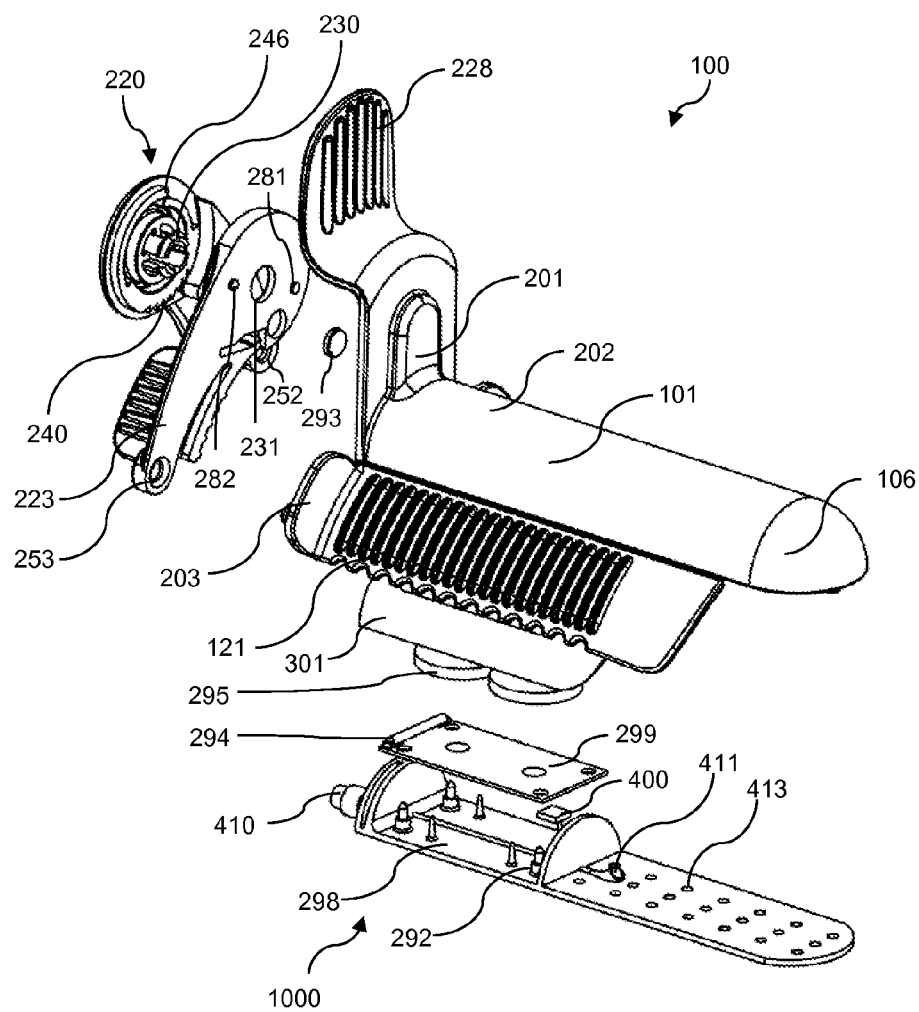
FIG. 8 is an exploded top view of the exemplary speculum of FIG. 7.
Figure 9:
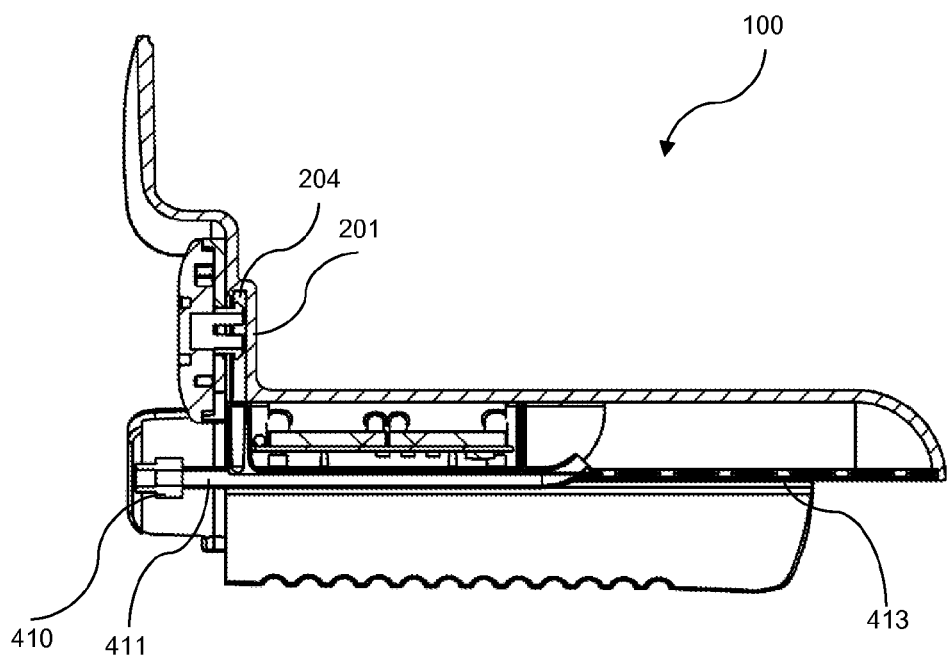
FIG. 9 is a cross-sectional side view of the exemplary speculum of FIG. 7 taken along the line 9-9' in FIG. 7.
Figure 10:
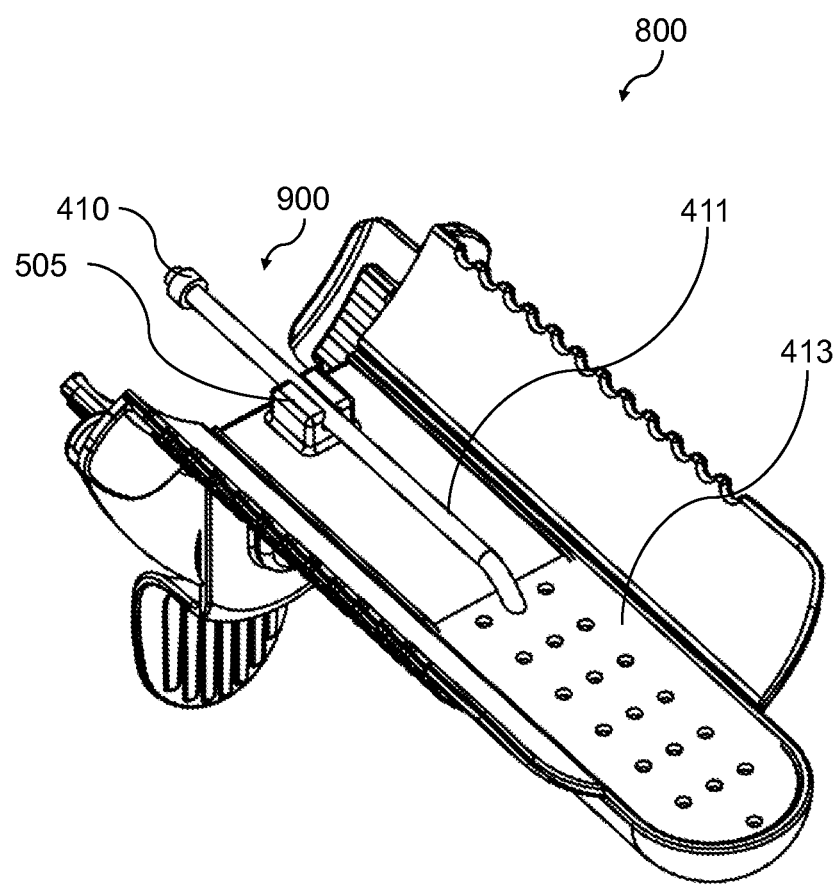
FIG. 10 is an isometric bottom view of the exemplary speculum of FIG. 7.
Figure 11:
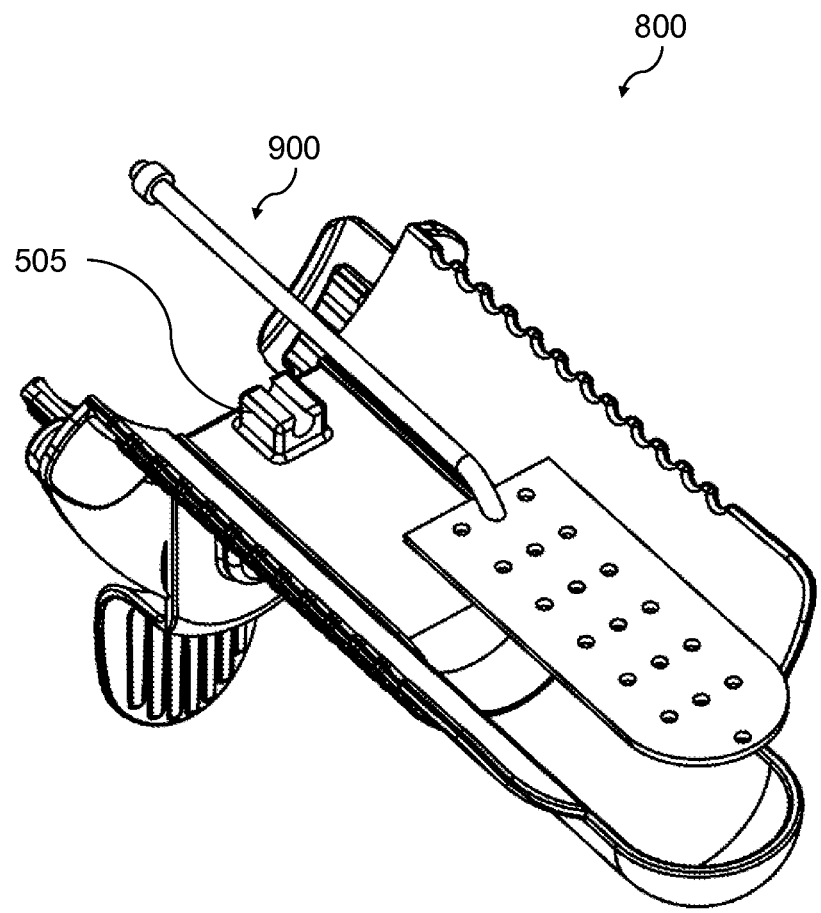
FIG. 11 is an exploded bottom view of the exemplary speculum of FIG. 7.
Figure 12:
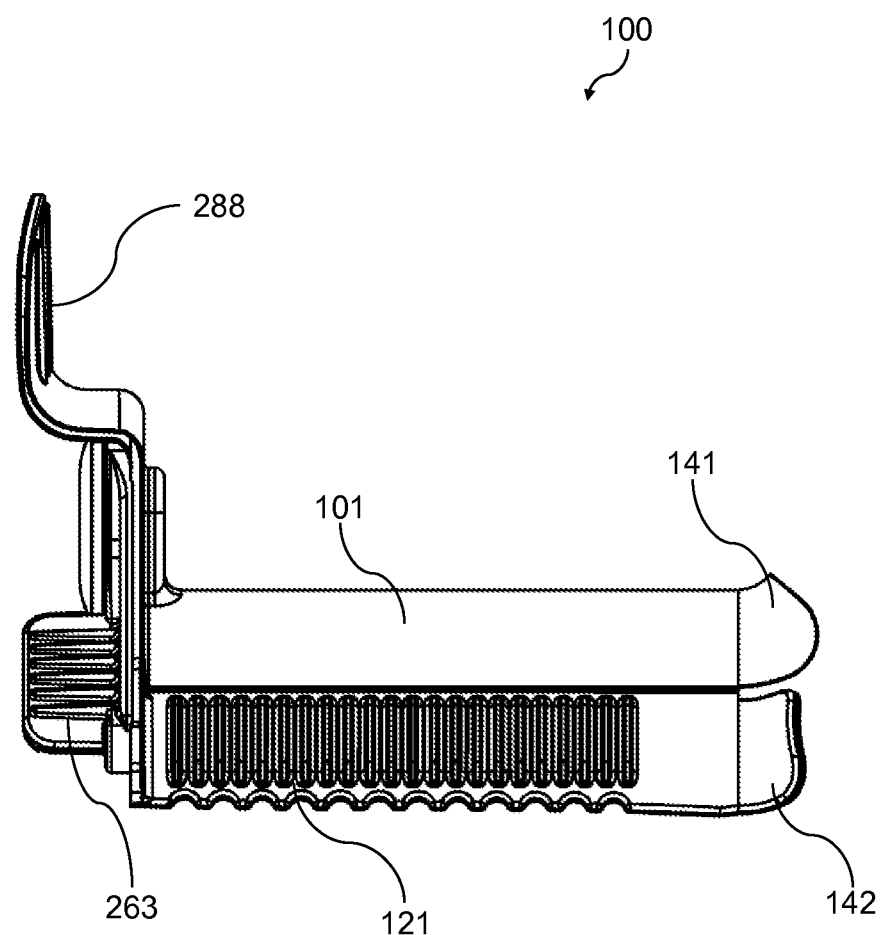
FIG. 12 is a side view of an exemplary speculum with a flared distal end.
Figure 13:
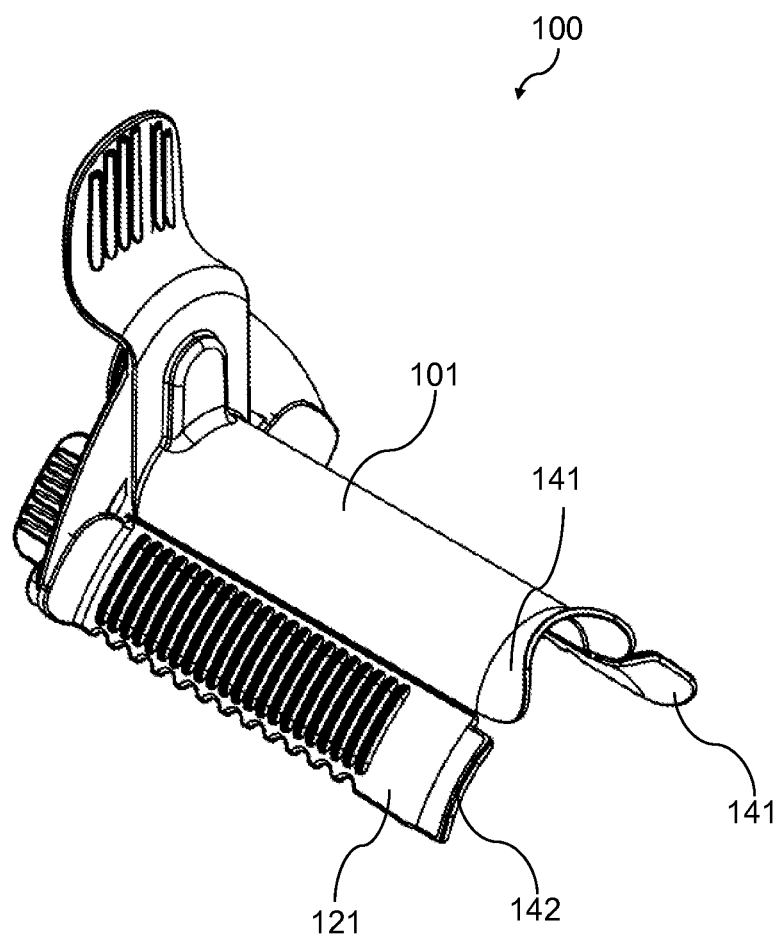
FIG. 13 is an isometric view of the exemplary speculum of FIG. 12.
Figure 14:
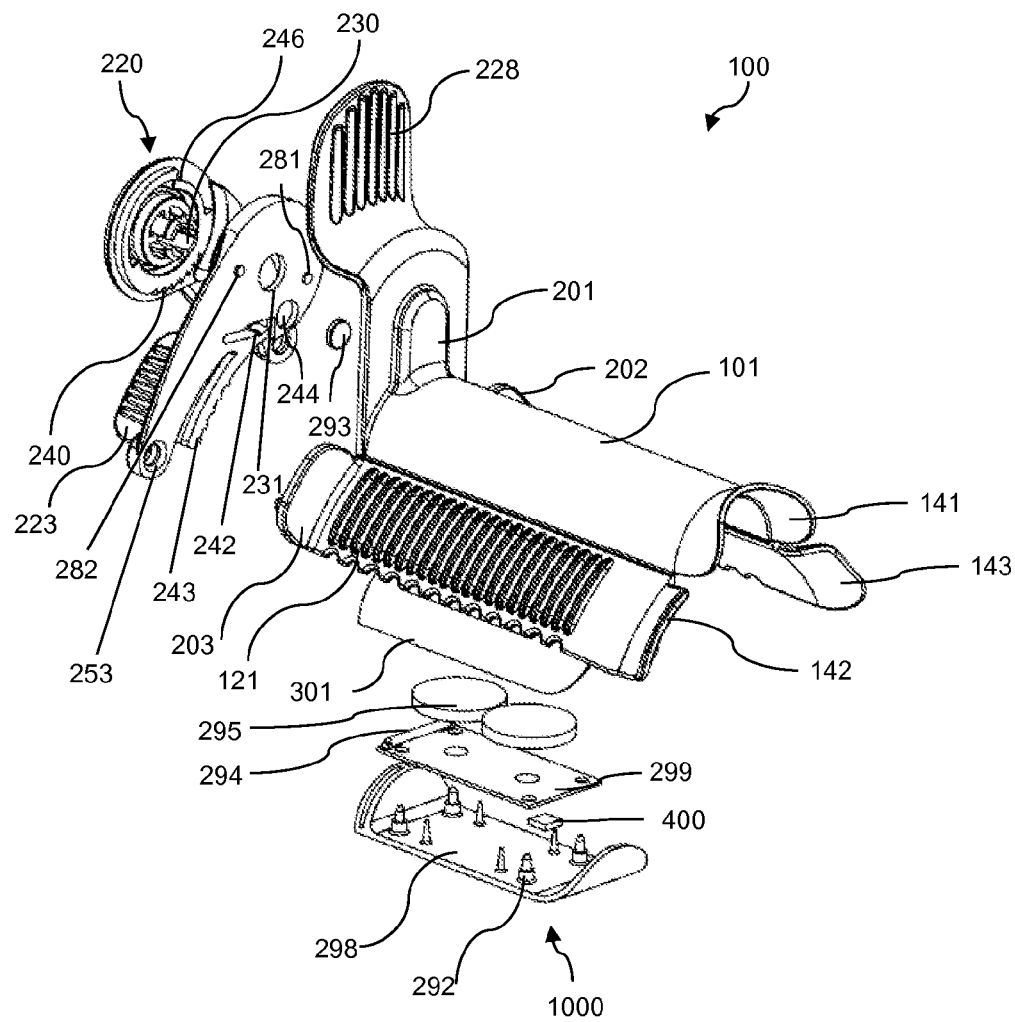
FIG. 14 is an exploded side view of the exemplary speculum of FIG. 12.

In one example, the speculum (100) may further comprise an illumination source (1000). Examples of the speculum comprising the illumination source (1000) are shown in FIGS. 2, 8, and 14.

In some examples, the fluid handler (900) may be permanently or temporarily attached to the structure of the illumination source (1000). The fluid handler (900) may be permanently attached to the structure of the illumination source, as shown in FIGS. 1-4, 7-8 and 15. The fluid handler (900) may be temporarily attached to the illumination source, as shown in FIGS. 5-6 and 10-11, by using the features disclosed above.

For example, the speculum (100) may comprise an illumination source (1000) and a fluid handler (900), wherein the fluid handler (900) may be permanently or temporarily the structure of the illumination source (1000). In another example, the fluid handler comprising a perforated conduit may be permanently or temporarily attached to the structure of the illumination source. Yet in another example, the perforated conduit comprising a non-perforated segment and a perforated segment may be temporarily or permanently the structure of the illumination source. Still another example, the perforated conduit comprising a tube with a perforated distal end may be temporarily or permanently attached to the structure of the illumination source. Also, in another example, the perforated conduit comprising a tube and a perforated plate may be permanently or temporarily attached to the structure of the illumination source.

The speculum (100) may further comprise a channel. For example, this channel may have any shape and size. In one example, this channel may have a concave shape. In another example, this channel may be a narrow depression such as trough or gutter. As disclosed above, the fluid handler (900) may help to reduce amount of fluids that may obscure inspection or interfere with a medical intervention. In such cases, the liquids may partially or substantially cover or flood the canopy formed by the central body portion (101), the at least one wing (102,103), and the at least one hinge (104,105). This may particularly happen when the user rotates the speculum within the vagina to medically intervene to the different vaginal surfaces. For such applications, the channel may aid easy removal of the liquid from the speculum and the vagina.

Figure 3:
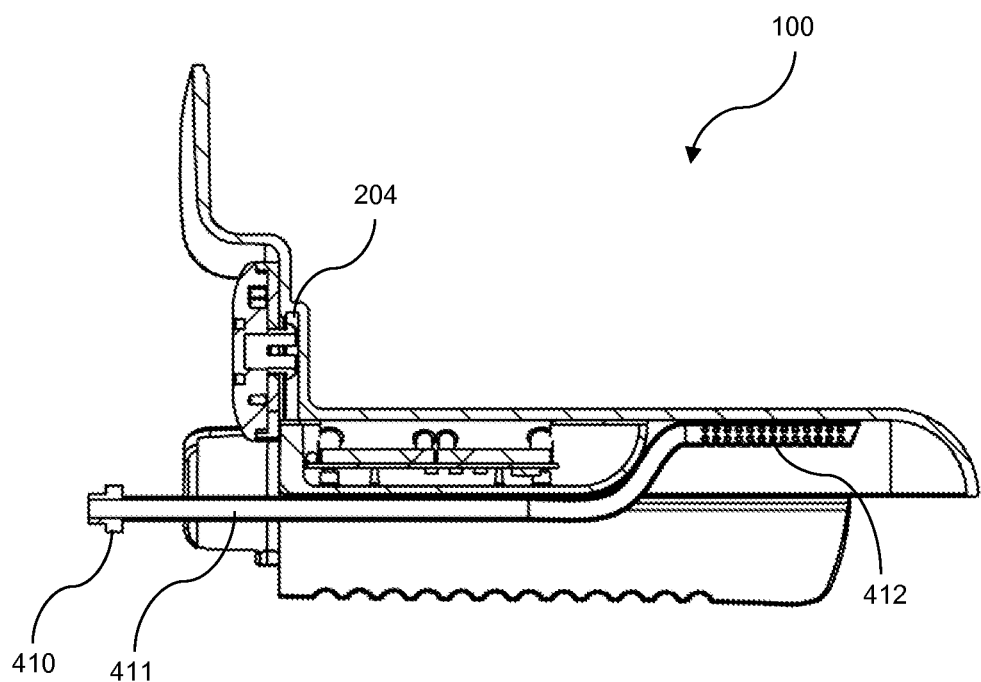
FIG. 3 is a cross-sectional side view of the exemplary speculum of FIG. 1 taken along the line 3-3' in FIG. 1.
Figure 4:
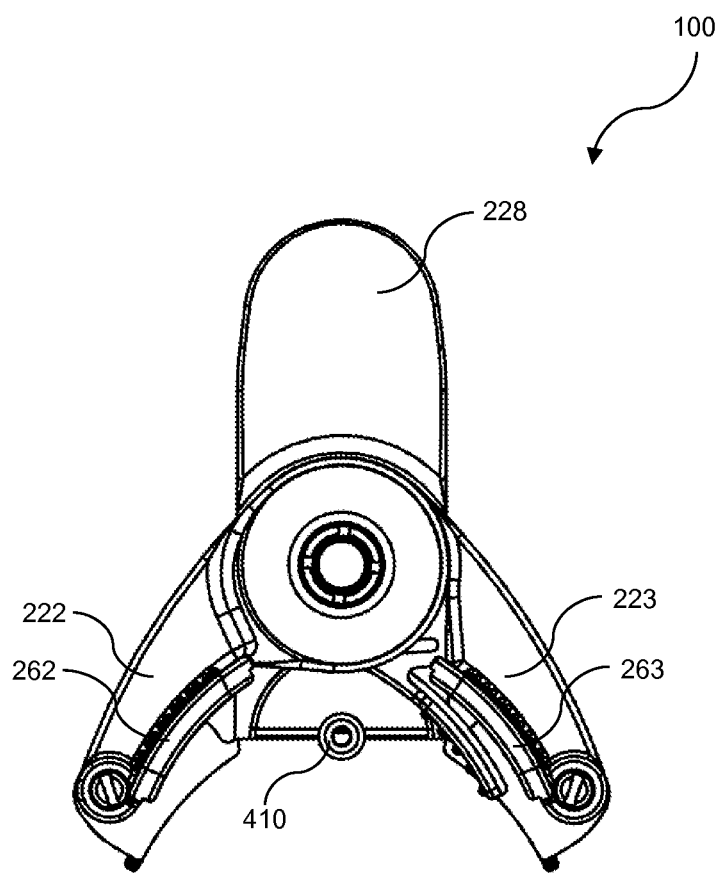
FIG. 4 is a front view of the exemplary speculum of FIG. 1

In one example, the channel may be integrated into the central body portion (101). For example, the central body portion facing the liquid handler (900) may have a concave shape, as shown in FIG. 3. In another example, the channel may be integrated into the fluid handler (900).

As disclosed above, the central body portion (101), the at least one wing (102 or 103), and the at least one hinge (104 or 105) may form a canopy. In some examples, the canopy may be formed such that the fluid flow through the exterior surface of the canopy, defined by the exterior surfaces of the body (101), wings (102,103) and hinges (104, 105), is substantially blocked.

The central body portion (101) may be convex on the exterior of the speculum (100) and concave on the interior. The central body portion (101) may be of a shape, contour, thickness, angle, radius, and size to hold up the vaginal walls during various procedures.

The wing (102,103) has a proximal end and a distal end. The wing (102,103) also has a top adjacent to the hinge (104,105) and a bottom. The wings (102, 103) may be solid. These wings (102,103) may also be hollow and shell-like to provide a convex exterior and conversely, a generally concave interior to permit visual as well as manual access thereto. The wings (102,103) may be of a shape, contour, thickness, angle, radius, and size to hold up the vaginal walls during various procedures.

The wings (102, 103) may also comprise protruded and/or thinned portions (120, 121) to provide friction and prevent the device (100) from undesirable movement during use. These thinned portions are thinner than the remaining portions of the wing. The protruded and/or thinned portions (120, 121) may protrude from the wings (102, 103) or be etched or carved into the wings. The protruded and/or thinned portions may be anywhere on the wings. The protruded and/or thinned portions may be on the edges of the wings. The protruded and/or thinned portions may comprise various shapes or forms such as grooves, serrations, crosshatches, bumps, or other morphologies to provide adequate friction with the tissue, while not damaging the tissue or causing discomfort to the patient. In other examples, the top portion of the central body portion (101) may comprise grooves, blunted barbs, or other textures to provide friction and to resist slippage of the speculum (100) within the vaginal cavity. In one example, the wings comprise serrated wing edges. This serrated wing edges may be at the bottom.

An example of the speculum (100) may comprise a so-called "living hinge". In this example, the speculum may be formed as one piece, by using manufacturing techniques such as molding, machining or welding. And the thinned section of the speculum, which is relatively thinner than the central body portion and the wings, forms the living hinge. Thereby, the one-piece speculum can easily flex along the line of the living hinge. A hinge of this type may be capable of many flexures over an extended period of time without the material fatiguing or breaking.

In one example, the width of the living hinge is smaller than the width of the wing (102,103) and/or the central body portion (101). In another example, the living hinge (104, 105) width is substantially smaller than the width of the wing (102,103) and/or the central body portion (101).

The living hinge (104,105) is not the only speculum example that has a canopy wherein the fluid flow through the exterior surface of the canopy is substantially blocked. Other examples are as follows. In one example, the speculum (100) may be formed by substantially reducing the width of the hinge and/or the width of the gap between the central body portion (101) and the wing (102,103). In another example, the wings (102,103) are formed to overlap on the exterior surface of the central body portion (101) or the central body portion (101) is formed to overlap on the exterior surface of the wings (102,103). Yet, in another example, the speculum (100) may further comprise a substantially impermeable membrane that substantially covers the exterior and/or the interior surface of the canopy, or the exterior and/or the interior surface of the gap between the central body portion (101) and the wings (102,103). In yet another example, the speculum (100) may further comprise at least one central body portion (101) and/or at least two wings (102,103) that are entirely or partially flexible such that the wings (102,103) may be able to move toward or away from each other by bending of the entire structure.

The hinges (104, 105) may comprise the same or different material as the wings (102, 103) and the central body portion (101). The hinges (104, 105) may permit the wings (102, 103) to flex or pivot about the central body portion (101) such that the lower longitudinal wing edges of the speculum may be pivoted open to permit visual and manual access to the interior of a body passage.

The exemplary speculum (100) may also comprise a ratchet mechanism (220). This ratchet mechanism (220) may serve to provide structural support to the wings (102, 103) to counteract the force of the vaginal walls on the wings. This structural support may also prevent the hinges (104, 105) from breaking due to the force of the vaginal walls on the wings (102, 103). The ratchet mechanism (220) may also serve to hold the wings (102, 103) in various positions with respect to each other. For example, the user may desire to have the wings (102, 103) closer to each other during insertion and removal of the speculum (100). Various wing positions may also be desired for different body shapes, sizes, or morphologies.

In some examples, the ratchet mechanism (220) may comprise two ratchet arms (222, 223). In some examples, the ratchet mechanism (220) may prevent the wings (102, 103) from moving toward each other from the force of the vaginal walls, while in other examples the ratchet mechanism (220) may lock together to prevent the wings (102, 103) from moving away from each other due to the configuration of the hinges (104,105). The ratchet arms (222, 223) may attach to three areas of the speculum (100): at the base of each wing's lip (202, 203) and at the speculum limiter (201). The lips (202, 203) may comprise fasteners (255, 256), which may comprise barbed pins that engage the fastener recesses (252, 253) of the ratchet arms (222, 223).

In other examples, the ratchet arms (222, 223) may further attach to the body of the speculum (100) by means of central ratchet hub fastener (230) protruding from the left speculum arm (222), as shown in FIG. 3. The ratchet hub fastener (230) may comprise barbed pins. The ratchet hub fastener (230) may pass through a hole (231) shown in FIG. 3.

The ratchet hub fastener (230) may also fasten to a limiter recess (204) on the proximal side of the speculum limiter (201). The limiter recess (204) may be elongated along its vertical axis in order to allow the fastener pin (230) to slide up and down along the vertical axis of the limiter. This sliding may be necessary as the ratchet arms (222, 223) move away from each other, since in this example the fasteners are fixed to the lips (202, 203).

In other examples, the limiter recess (204) may not be elongated, so that the fastener pin (230) would not move up or down with respect to the speculum limiter (201). Rather, the fastener recesses (252, 253) of the ratchet arms (222, 223) could be elongated so that the fasteners are fixed to the lips (202, 203) and could move along the elongated fastener recesses.

The ratchet arms (222, 223) may also comprise ratchet grasps (262, 263). The ratchet grasps (262, 263) may be useful for spreading the ratchet arms away from, or closer to, each other. The ratchet grasps (262, 263) may also be useful for altering the position of the speculum (100), inserting the speculum, or removing the speculum. The ratchet grasps (262, 263) may further comprise textures, or other protruded and/or thinned portions, in order to increase friction and facilitate gripping by the user. One of the ratchet arms (222, 223) may comprise a ratchet release trigger that comprises a ratchet release trigger handle (243) and a ratchet tooth engager (242). The ratchet tooth engager (242) may latch onto the ratchet teeth (240) of the other ratchet arm. The ratchet tooth engager (242) may release from the ratchet teeth (240) when the user presses the ratchet release trigger handle (243).

A carve-out adjacent to the ratchet teeth may serve as a ratchet limiter engaging slot (246) along which a ratchet limiter stop on the opposing ratchet arm may move as the ratchet arms move relative to each other. This may prevent the distance between the tips of the of the ratchet arms (222, 223) from exceeding three inches. In some examples, the distance may be more than three inches, for instance about four inches. In other examples, it may be 2.5 inches or less.

To stabilize the sliding motion of the main body relative to the ratchet arms, one of the ratchet arms (222, 223) may comprise two pegs (281,282) which are able to travel back and forth within mating grooves (291, 292) integrated within the central body portion (101), thereby effectively restricting rotation of the speculum (100) off axis, swiveling of the central body portion (101) relative to the ratchet arms, and/or buckling of the hinges (104, 105).

The exemplary speculum (100) may also comprise a distal tip (106), which is the first part of the speculum inserted into the body. The distal tip (106) may be thick and wide enough to hold the upper portion of the vaginal walls during various procedures.

The distal end of the distal tip (106) may be round and smooth to provide comfort and minimize damage to the tissue during use. In some examples, the distal tip (106) may comprise only slightly concave, straight, or convex portion such that the open distal tip (106) provides a clear and open view of the cervix. This slightly concave distal tip (106) may resemble a duck-bill in shape, common to existing vaginal speculum designs. In some examples, the distal tip (106) may also comprise grooves, blunted barbs, or other textures to provide friction and to resist slippage of the speculum (100) within the vaginal cavity. In some examples, the distal tip (106) may have a slight curvature suitable to positioning in the vaginal fornices. This positioning of the distal tip (106) in the vaginal formix may help to ensure that a clear, unobstructed view of the cervix is provided.

The speculum (100) may further comprise a gripping proximal tip (228) at the proximal end. This gripping proximal tip may extend from the proximal end of the central body portion (101). This gripping proximal tip may stick out of the vagina while the rest of the speculum is inserted, and thus allow the user to grab the portion to facilitate altering the position of the speculum (100), inserting the speculum, removing the speculum, or holding the speculum in place. This gripping proximal tip may further comprise textures, or other protruded and/or thinned portions, in order to increase friction and facilitate gripping by the user.

In some examples, the speculum (100) comprises a speculum limiter (201). The limiter (201) may be included in the same molded part as the central body portion (101). The limiter (201) may prevent the speculum (100) from penetrating too far into vagina, and may prevent damage to the cervix, uterus, or other parts of the female patient. The limiter (201) may also have a smooth surface free of surface protrusions or holes in order to prevent painful interaction with the clitoris.

The wings (102, 103) may also comprise lips (202, 203) at their proximal ends. The lips (202, 203) along with the wings (102, 103), the central body portion (101), and the limiter (201) may prevent blood, tissue, or other materials from entering the area where the suturing takes place. The lips (202, 203) may also help to prevent the speculum (100) from penetrating too deeply into the vagina. The lips (202, 203) may also increase stability of the speculum (100), and help to secure its position with respect to the vagina.

The wings (102, 103) may flare outward along a portion of their length. In particular, distance between the opposing wings may be greater toward the end that is deeper the body cavity, and may be narrower toward the opening of the vaginal cavity. Consequently, pressure of the vaginal walls upon the length of the speculum's blades may tend to hold the speculum (100) within the cavity, thereby preventing the speculum (100) from sliding out of the vagina.

In one example, the speculum (100) may further comprise a serrated edge (121), as shown in FIGS. 1-15. The serrated edge (121) may prevent undesired movements, such as slippage, of the speculum (100) when it is placed in the vagina.

As disclosed above, in some examples, the speculum (100) may further comprise an illumination source (1000). The illumination source may comprise more than one illumination devices.

In other examples, one or all device components forming the illumination source may be located within the speculum limiter (201). In one example, a fiber optic cable or light-guide may direct the light to one or more sites where the light is emitted. The fiber optic cable or light-guide may refract the light for focused or diffuse emission. Yet, in another example, one or all device components forming the illumination source may be located within the canopy formed by the speculum (100). For example, the illumination source (1000) may comprise a light-emitting diode wherein the light emitting diode may be located within the speculum canopy. Also, in another example, the whole illumination source is located within the speculum canopy. In such examples, a compact speculum (100) with no illumination source components dangling beyond the other speculum parts may be obtained.

One example the illumination source (1000) may comprise a light, such as battery-powered light-emitting diode (LED), located within a light source housing. In some examples, the light source housing may be attached to a cap (not shown) that attaches to the speculum limiter (201). The cap may attach to the limiter by means of a fastener, comprising a pin, which connects to either a ratchet arm (222, 223) or the speculum limiter (201). In some examples, the cap does not have a fastener; rather it may attach by means of an adhesive. In some examples, the light source housing may swivel. In some examples, the user may manually operate the light function externally via a mechanical switch, while in another examples, the light function may be turned on and off automatically. In some examples, the user may control the brightness of the light. In one example, the user may control the brightness of the light by means of a switch, button, or dial.

In other examples, as shown in FIGS. 1-15, the illumination source (1000) may comprise a plurality of light emitting components such as light emitting diodes (LEDs) (400) capable of producing sufficient visible light to view the area of interest, a power supply such as coin cell batteries (295) to drive the LED (400), power management components such as resistors, and reed sensor switch (294) to activate the LED (400). The LED (400), resistors, reed switch (294) and power supply batteries (295) may be assembled on a printed circuit board (299), also known as a PCB. Alternatively, the light may be emitted by electroluminescent or chemiluminescent material.

In yet other examples, the illumination source may be automatically turned on and off in conjunction with movement of the ratchet arms (222, 223) away from, and towards, each other, respectively.

In the exploded view of the exemplary speculums shown in FIG. 2 and FIG. 8, the LED may be turned on and off via a reed sensor switch (294). The reed sensor switch (294) may be turned on in the presence of a magnetic field generated by a magnet (293), and may turn off in the absence of the magnetic field generated by the magnet. The reed sensor switch (294) may be sensitive to the position of the magnet (293). The magnet (293) may be installed within a magnet seat (244), which may be located in one of the ratchet arms (222, 223).

The coin cell batteries (295) may be connected using contact wires or directly assembled onto the printed circuit board (299). Alternatively, the electronic components may be brought in contact to complete the circuit without soldering and connected by compression of the assembly packaging.

The LED assembly may be placed onto a plurality of mounting posts (297) on an LED cover (298), which may comprise a translucent material, and assembled into mating features (not shown) located on the underside of the central body portion (101).

A gasket (301) made of rubber or other materials, may be placed between the LED cover (298) and an inner surface of the central body portion (101) to prevent or minimize the ingress of fluids and dirt into the LED assembly. In addition, in the case of leaking power supply batteries, the gasket (301) may prevent chemicals from leaking outside the speculum (100), thereby protecting the user. The gasket (301) may be held in place by mating features in the main body surface, by adhesive, or by other means.

The LED covers (298) and LED assembly may also be mated with the main body via other fastening mechanisms such as screws or epoxy.

The stem may travel in a vertical path inside a slot located with the LED cover (298), thereby making the actuation mechanism hidden from to the user.

In another example, the magnet (293) may be embedded within or attached to one of the ratchet arms (222, 223).

In another example (not shown), the mechanism of turning the light on and off may comprise a mechanical push button switch. The switch may be placed behind the ratchet arms at a location where the arms interact with each other. When the ratchet arms are opened outward and pass over each other, the switch may be triggered, thus completing the electrical circuit and turning on the light.

In another example, the mechanical push button switch may be placed between surfaces of the ratchet arms where the mechanical push switch button may by pressed in the off position when the ratchet arms (222, 223) are closed, thus keeping the light function off. When the ratchet arms (222, 223) are opened outwardly, this may release the switch, thereby turning the switch to the on position, completing the electrical circuit and turning the light function on.

Alternatively, the mechanical push button switch may be accessible to the user to manually turn the light function on or off. The switch may be located on the ratchet arm hub for easy access.

In another example, an optical sensor switch may be used to activate the light function. The switch may be placed in the main body or ratchet arm and between the surfaces thereby occluding the sensor of the switch from ambient light. When the ratchet arms (222, 223) pass over and expose the optical sensor, the switch turns the light function on.

In another example, a breakoff plastic feature may be used to trigger a switch (or an incomplete circuit by a separated wire connection) to turn on the light. In the closed position, one of the ratchet arms (222, 223) may be connected to the switch via a plastic feature or tab. When the ratchet arms (222, 223) are pulled outward to open the wings, this plastic tab could break, consequently activating the switch (or completing the connection between the separated wire) to turn on the light. With this mechanism, the device light function could stay on until the batteries are drained of their power. A variation of this mechanism may use the plastic tab as a cover over the optical sensor switch. On pulling the ratchet arms outwardly, the plastic tab could break and expose the optical sensor, thereby completing the electrical circuit and turning the light on.

In other examples, the device may comprise a plurality of LEDs located at various portions of the interior of the device. For example, the LEDs may be located on or integrated within the interior surfaces of the central body portion (101), the distal tip (106), and/or the wings (102, 103).

In yet other examples, the speculum (100) may comprise only two wings (102,103) and only one central body portion (101). That is, the speculum may not have more than two wings and may not have more than one central body portion.

In some examples, the speculum (100) may be manufactured from a material that may comprise a polymer such as acrylonitrile butadiene styrene (ABS), polyurethane, acetal plastics, or another material known to those skilled in the art that provides both structural rigidity and flexibility. This material may also comprise flexible plastic material such as polyamide sold under the trade name "Nylon," polytetrafluoroethylene sold under the trademark "Teflon". Alternatively, a polypropylene plastic or a high density polyethylene plastic may be used to manufacture the speculum (100). The speculum (100) may be made of a transparent plastic in order to enhance the viewing area. It may also be made of metal. Mixtures or composites of these materials may also be used to manufacture the speculum (100).

The hinge (104,105) may be manufactured from a material that may comprise a polymer. The hinge, for example, may be made from a material comprising polyethylene, polypropylene, nylon, acetal plastics or mixtures thereof. In another example, the hinge material may even be manufactured from a material comprising polyethylene, polypropylene or mixtures thereof.

The speculum (100) may be sterilizable by ethylene oxide, gamma radiation or other process known to those skilled in the art. It may be disposable or reprocessable. Also, the speculum (100) may be made of different sizes and/or thicknesses to accommodate different ages and sizes of patients. The speculum (100) may be coated with a material to facilitate inspection and movement. For example, a lubricant can be used to coat the speculum (100) to facilitate insertion and retrieval.

In some examples, a significant portion of the speculum (100) may be formed from a single continuous material. That is, the speculum—is formed from only one component. In these examples, the speculum may be manufactured by molding. For example, the central body portion (101), wings (102, 103), and distal tip (106) may be injection molded to form a single component. An exemplary material for injection molding may be polypropylene.

In some examples, the speculum (100) may be sized to fit vaginas of different size ranges. In other examples, the speculum (100) may be sized to fit larger vaginas. In some examples, the speculum's dimensions and contours may accommodate the excess tissue of overweight and obese patients. These variations may consist of differences in any of a variety of dimensions of the speculum and its features, such as the overall length of the speculum (100); the length and/or width of the central body portion (101); and/or the span, length, shape, and/or morphology of the wings (102, 103).

The speculum (100) may be used in various procedures, including episiotomy repair, repair of vaginal lacerations, and visualization during checkups. For example, the ratchet mechanism may be adjusted to hold the wings (102, 103) in various positions with respect to each other. For example, the user may desire to have the wings (102, 103) closer to each other during insertion and removal of the speculum (100), while keeping the wings (102, 103) farther apart from each other to maximize the viewing and working fields during procedures. Various positions may also be desired for different body shapes, sizes, or morphologies. The position of the wings may be changed during procedures using the ratchet mechanism.

The speculum (100) may be used for improved visualization, access, and repair in various procedures, including, but not limited to: obstetrical/gynecological procedures: vaginal inspection; perineal inspection; vaginal wound repair; perineal wound repair; episiotomy repair; female pelvic exam; pap smear; cervical biopsy; vaginal/pelvic reconstruction; urological procedures; colorectal, general, or other surgery; the speculum (100) may be turned upside-down, for example, for female urologic procedures; access to the cervix (or uterus via cervix); IUD insertion, removal, or adjustment; colposcopy, speculoscopy, and dilatation & curettage (dilatation of cervix and curettage of uterus).

A vaginal laceration typically has its apex nearer the cervix and become wider toward the introitus. In using the speculum (100), the user may begin suturing a vaginal laceration with the speculum (100) deployed in the vagina in its open position, with the speculum (100)'s wings (102, 103) spread apart. The suture is typically started at the apex of a tear deeper in the vagina, nearer the vaginal vault or cervix. While proceeding to suture and moving toward the introitus, where the tear is typically wider than at its deeper apex, the user may adjust the speculum (100) to a more closed position, with its wings (102, 103) closer to each other. This may ease the approximation of tissue from opposing sides of the laceration. Intermittent, slight closing of the speculum (100) as the suturing is performed may allow the user to achieve the appropriate degree of retraction throughout the run of the suture, until the suturing is complete.

The speculum (100) and the system (800) may be used in a variety of medical and surgical procedures including vaginal and perineal wound repair, episiotomy repair, pelvic floor repair and/or reconstruction, and/or cosmetic gynecology procedures.

In other examples, the speculum (100) may comprise a plurality of LEDs located at various portions of the interior of the device. For example, the LEDs may be located on or integrated within the interior surfaces of the central body portion (101), the distal tip (106), and/or the wings (102, 103). In other examples, the speculum (100) may comprise LEDs of different colors, with a switch mechanism that allows the user to switch between different colors of illumination. In yet other embodiments, the speculum (100) may comprise one or more colored transparent/translucent material swatches or lenses that the user may move into or out of the path of the light. For example, this color switching mechanism may comprise a spinnable wheel with differently colored segments, a slidable window with differently colored segments, or insertable and removable panels of different colors. In one example, the speculum may allow the user to control different settings of illumination, which may include white light, green light, different brightnesses of light, and no light.

In some examples, the speculum may comprise a magnifying lens. The magnifying lens may be integrated with the body of the device, or may be a separate attachment. For example, the reservoir may be located on, or integrated within, the proximal end of the central body portion (101) and/or the wings (102, 103). In some examples, the magnifying lens may further comprise a latch for user to apply or remove it from the device, or a sliding mechanism for moving the magnifying lens into or out of view. The magnifying lens may provide the user with a magnified view of the cervix or other anatomic, pathologic, or other structures.

Figure 15:
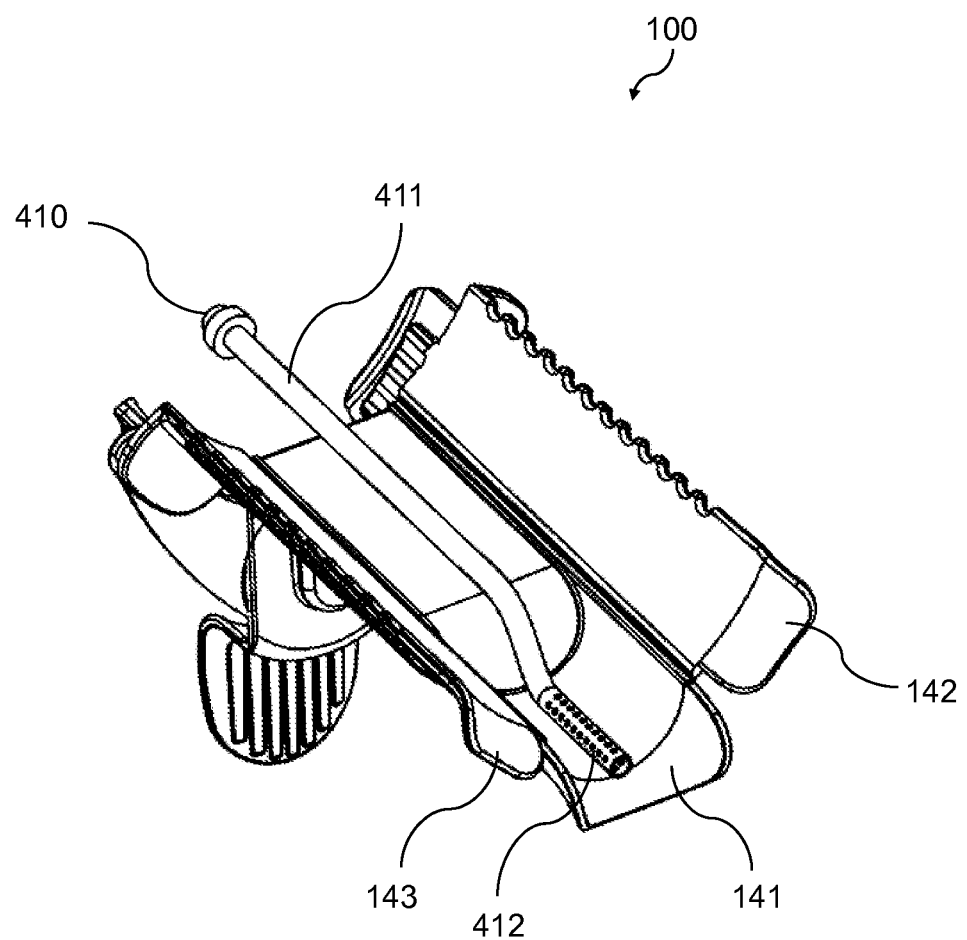
FIG. 15 is a view of an exemplary speculum with a flared distal end and a fluid handler.

FIGS. 12-15 depict various views of other exemplary specula (100). This speculum may be used as a retractor for the surgical incisions. In one example, the central body portion (101) and/or wings (103) may flare inward along a portion of their length. In particular, distance between the opposing wings may be narrowed toward the middle of the wings. Alternatively, the proximal and/or distal ends of the central body portion and/or wings may flare outward. Alternatively, the distal ends of the central body portion and/or wings may have protrusions, such as ridges, on their exterior surfaces. In the exemplary speculums shown in FIGS. 12 to 15, the central body portion comprises a ridge (141) at its distal end, and the wings comprise ridges (142, 143) at their distal ends. Consequently, pressure of the retracted tissue layers upon the length of the device's central body portion and/or wings, on the narrower segments between the flares or protrusions at their distal an/or proximal ends, may tend to hold the speculum within the surgical opening, thereby preventing the device from sliding out of the surgical opening. Thus, the device would effectively grasp the incised tissue layers in a manner similarly to a split grommet securely spanning a hole in a membrane. In one example, the speculum may further comprise a fluid handler as shown in FIG. 15.

The exemplary specula shown in FIGS. 12-15 may be used for improved visualization, access, and repair in various procedures, including, but not limited to: obstetrical/gynecological, urological procedures, colorectal, general, or other surgery. For examples, the device may be used in: tubal ligation; salpingo oophorectomy; thyroidectomy; video-assisted thoracoscopic surgery; thoracotomy; appendectomy; myomectomy; lap colectomy; colposcopy, speculoscopy, and mini-laparotomy.

Any combination of features and/or embodiments of the speculum and the method of its use disclosed above is within the scope of this disclosure. For example, the speculum (100) may comprise a central body portion, at least two wings, at least two hinges that affix the at least two wings to the central body portion, and a fluid handler; wherein the fluid handler is a temporarily attachable fluid handler, and wherein the docking port may be used to attach the temporarily attachable fluid handler to the speculum; wherein the fluid handler comprises a perforated conduit, and wherein the perforated conduit comprises a non-perforated segment and a perforated segment. For example, the speculum (100) may comprise a central body portion, at least two wings, at least two hinges that affix the at least two wings to the central body portion, and a fluid handler; wherein the fluid handler is a temporarily attachable fluid handler; and wherein the docking port may be used to attach the temporarily attachable fluid handler to the speculum; wherein the fluid handler comprises a perforated conduit; wherein the perforated conduit comprises a non-perforated segment and a perforated segment; and wherein the speculum further comprises a channel integrated with the central body portion.

The previous description of embodiments is provided to enable any person skilled in the art to make or use the speculums. Various modifications to these embodiments will be readily apparent to those skilled in the art, and the generic principles defined herein may be applied to other embodiments without departing from the spirit or scope of the speculums. Thus, the speculums are not intended to be limited to the embodiments shown herein but are to be accorded the widest scope consistent with the principles and novel features disclosed herein.

The components, steps, features, objects, benefits and advantages which have been discussed are merely illustrative. None of them, nor the discussions relating to them, are intended to limit the scope of protection in any way. Numerous other embodiments are also contemplated. These include embodiments which have fewer, additional, and/or different components, steps, features, objects, benefits and advantages. These also include embodiments in which the components and/or steps are arranged and/or ordered differently.

Unless otherwise stated, all measurements, values, ratings, positions, magnitudes, sizes, and other specifications which are set forth in this specification, including in the claims which follow, are approximate, not exact. They are intended to have a reasonable range which is consistent with the functions to which they relate and with what is customary in the art to which they pertain.

All articles, patents, patent applications, and other publications which have been cited in this disclosure are hereby incorporated herein by reference.

Nothing which has been stated or illustrated is intended or should be interpreted to cause a dedication of any component, step, feature, object, benefit, advantage, or equivalent to the public, regardless of whether it is recited in the claims.

We claim:
1. A system, comprising:
a speculum having a proximal end, a distal end, an exterior surface, and an interior surface, comprising:
a central body portion,
at least two wings,
two hinges, each hinge configured to affix a different one of the at least two wings to the central body portion, and
a ratchet mechanism that releasably locks the wings in an open position; and
a fluid handler affixed to the speculum,
wherein the wings are rotatable about the hinges when moving from a closed position to an open position;
wherein the fluid handler comprises a conduit, wherein the conduit comprises a perforated segment, wherein the perforated segment comprises a plurality of holes about a circumference of the conduit, and the perforated segment extends along a direction formed by the distal end of the speculum and the proximal end of the speculum;
wherein the fluid handler is configured to remove fluid from or deliver fluid to tissue in the vicinity of the speculum and/or along the perforated segment during use;
wherein the wings, the hinges, and the central body portion form a canopy that creates and only partially surrounds an interior space that is not surrounded by any other portion of the speculum when the wings are in the open position; and
wherein no portion of the speculum obstructs any portion of a length of the interior space opposite the central body portion between the proximal end and the distal end when the wings are in the open position.

2. The system of the claim 1, wherein the fluid handler is configured to remove the fluid from the tissue in the vicinity of the speculum and/or along the perforated segment during use.

3. The system of the claim 1, wherein the fluid handler is configured to deliver the fluid to the tissue in the vicinity of the speculum and/or along the perforated segment during use.

4. The system of the claim 1, wherein the fluid handler is affixed to the central body portion.

5. The system of the claim 1, wherein the fluid handler is affixed to at least one of the at least two wings.

6. The system of the claim 1, wherein the system further comprises an illumination source and wherein the fluid handler is attached to the illumination source.

7. The system of the claim 1, wherein the conduit comprises a non-perforated segment.

8. The system of the claim 7, wherein the conduit comprises a tube with a perforated distal end.

9. The system of the claim 1, wherein the speculum further comprises a docking port, wherein the fluid handler comprises a temporarily attachable fluid handler, and wherein the docking port attaches the temporarily attachable fluid handler to the speculum.

10. The system of the claim 1, wherein the speculum further comprises a channel, and wherein the fluid handler comprises a conduit, and wherein the conduit comprises a non-perforated segment and a perforated segment.

11. The system of the claim 10, wherein the central body portion forms at least a portion of the channel.

12. The system of the claim 10, wherein the fluid handler forms at least a portion of the channel.

13. The system of claim 1, wherein the speculum does not have more than two wings and does not have more than one central body portion.

14. The system of claim 1, wherein the central body portion has a distal end, wherein each wing has a distal end, and wherein the distal end of the central body portion and/or the distal end of the wings flare outward.

15. The system of claim 14, wherein the system further comprises a fluid handler affixed to the central body portion, and or to at least one wing.

16. The system of claim 14, wherein the speculum does not have more than two wings and does not have more than one central body portion.

17. The system of claim 1, wherein the fluid handler is positioned under the canopy.

18. The system of claim 17, wherein the fluid handler is affixed to the central body portion.

19. The system of the claim 17, wherein the fluid handler is affixed to one of the at least two wings.

20. The system of claim 1, wherein the perforated segment extends between the distal end and the proximal end of the speculum.

21. The system of the claim 1, wherein the fluid handler is affixed to the central body portion or one of the at least two wings.

* * * * *